(12) United States Patent
Fuimaono

(10) Patent No.: US 6,852,120 B1
(45) Date of Patent: Feb. 8, 2005

(54) IRRIGATION PROBE FOR ABLATION DURING OPEN HEART SURGERY

(75) Inventor: Kristine B. Fuimaono, Covina, CA (US)

(73) Assignee: Biosense Webster, Inc, Diamond Bar, CA (US)

( * ) Notice: Subject to any disclaimer, the term of this patent is extended or adjusted under 35 U.S.C. 154(b) by 0 days.

(21) Appl. No.: 09/370,601

(22) Filed: Aug. 10, 1999

(51) Int. Cl.$^7$ ................................................ A61F 7/00
(52) U.S. Cl. ............... 607/104; 607/116; 607/119; 607/101; 604/22; 606/41; 606/49
(58) Field of Search ................... 604/22, 20, 21, 604/43, 44, 95.02, 95.05, 95.04, 113, 114, 532; 607/116, 102, 104, 101, 113, 115, 119, 122; 606/41, 46, 45, 43, 47, 48, 50, 32; 600/152, 139, 144

(56) References Cited

U.S. PATENT DOCUMENTS

| | | | |
|---|---|---|---|
| 4,532,924 A | | 8/1985 | Auth et al. |
| 5,122,137 A | | 6/1992 | Lennox |
| 5,197,963 A | | 3/1993 | Parins ........................... 606/46 |
| 5,267,994 A | * | 12/1993 | Gentelia et al. ............... 606/15 |
| 5,329,923 A | * | 7/1994 | Lundquist .................... 128/642 |
| 5,342,357 A | | 8/1994 | Nardella |
| 5,348,554 A | | 9/1994 | Imran et al. |
| 5,413,575 A | * | 5/1995 | Haenggi ....................... 606/45 |
| 5,433,708 A | * | 7/1995 | Nichols et al. .............. 604/113 |
| 5,437,662 A | * | 8/1995 | Nardella ....................... 606/38 |
| 5,462,521 A | | 10/1995 | Brucker et al. ............... 604/20 |
| 5,605,539 A | * | 2/1997 | Buelna et al. ............... 604/508 |
| 5,643,197 A | | 7/1997 | Brucker et al. ............... 604/20 |
| 5,658,278 A | | 8/1997 | Imran et al. .................. 606/41 |
| 5,688,267 A | | 11/1997 | Panescu et al. ............... 606/41 |
| 5,700,262 A | * | 12/1997 | Acosta et al. ................. 606/48 |
| 5,735,846 A | | 4/1998 | Panescu et al. ............... 606/41 |
| 5,913,854 A | * | 6/1999 | Maguire et al. ............... 606/41 |
| 5,913,856 A | * | 6/1999 | Chia et al. ..................... 606/41 |

(List continued on next page.)

FOREIGN PATENT DOCUMENTS

| | | |
|---|---|---|
| DE | 24074559 A1 | 2/1975 |
| EP | 0105677 B1 | 12/1986 |
| EP | 0246350 A1 | 11/1987 |
| EP | 0274118 B1 | 7/1988 |
| EP | 0368161 A2 | 5/1990 |
| EP | 0480639 A2 | 4/1992 |
| EP | 0608609 B1 | 9/2001 |
| WO | WO 94/10924 | 5/1994 |
| WO | WO 94/11059 | 5/1994 |
| WO | WO 95/05212 | 2/1995 |

OTHER PUBLICATIONS

Haines, D.E., Watson, D.D., Verow, A.F., "Electrode Radius Predicts Lesion During Radiofrequency Energy Heating. Validation of a Proposed Thermodynamic Model," CIRC RES 1990; vol. 67, pp. 124–129.

Sanchez, R., et al., "Percutaneous Tissue Ablation by Radiofrequency Thermal Energy as a Prelim to Tumor Ablation," Minimally Invasive Therapy 1993, vol. 2, pp 299–305.

(List continued on next page.)

*Primary Examiner*—Nicholas D. Lucchesi
*Assistant Examiner*—Cris L. Rodriguez
(74) *Attorney, Agent, or Firm*—Christie, Parker & Hale, LLP

(57) ABSTRACT

An irrigation ablation probe comprises a generally rigid probe body and a handle mounted to the proximal end of the probe body. The generally rigid probe body comprises an ablation electrode at its distal end having at least one irrigation opening through which fluid can pass. An infusion tube extends through the probe body for introducing fluid into the ablation electrode. The irrigation ablation probe is useful for treating atrial fibrillation during open heart surgery.

56 Claims, 5 Drawing Sheets

U.S. PATENT DOCUMENTS

| | | | | |
|---|---|---|---|---|
| 5,919,188 A | * | 7/1999 | Shearon et al. | 606/41 |
| 5,951,546 A | * | 9/1999 | Lorentzen | 606/41 |
| 5,997,532 A | * | 12/1999 | McLaughlin et al. | 606/41 |
| 6,002,956 A | * | 12/1999 | Schaer | 600/381 |
| 6,010,500 A | * | 1/2000 | Sherman et al. | 606/41 |
| 6,015,407 A | * | 1/2000 | Rieb et al. | 606/41 |
| 6,017,338 A | * | 1/2000 | Brucker et al. | 606/41 |
| 6,032,077 A | * | 2/2000 | Pomeranz | 607/101 |
| 6,033,403 A | * | 3/2000 | Tu et al. | 606/41 |
| 6,056,745 A | * | 5/2000 | Panescu et al. | 606/42 |
| 6,080,151 A | * | 6/2000 | Swartz et al. | 606/45 |
| 6,080,152 A | * | 6/2000 | Nardella et al. | 606/46 |
| 6,102,046 A | * | 8/2000 | Weinstein et al. | 128/898 |
| 6,109,268 A | * | 8/2000 | Thapliyal et al. | 128/898 |
| 6,120,476 A | * | 9/2000 | Fung et al. | 604/95 |
| 6,146,380 A | * | 11/2000 | Racz et al. | 606/41 |
| 6,161,543 A | * | 12/2000 | Cox et al. | 128/898 |
| 6,176,857 B1 | * | 1/2001 | Ashley | 606/32 |
| 6,208,881 B1 | * | 3/2001 | Champeau | 600/374 |
| 6,210,406 B1 | * | 4/2001 | Webster | 606/41 |
| 6,231,591 B1 | * | 5/2001 | Desai | 606/210 |
| 6,238,389 B1 | * | 5/2001 | Paddock et al. | 606/41 |
| 6,270,476 B1 | * | 8/2001 | Santoianni et al. | 604/95.04 |

OTHER PUBLICATIONS

Goldberg, S.N., et al., "Tissue Ablation with Radiofrequency Using Multiprobe Arrays," ACAD RADIOL., 1995, vol. 2, pp 670–674.

Goldberg, S.N., et al., "Saline–Enhanced RF Tissue Ablation: Demonstration of Efficacy and Optimization of Parameters," RADIOLOGY, 1995, 197(P): 140 (abstr.).

Reidenbach, H.D., "First Experimental Results with Special Applicators for High–Frequency Interstitial Thermotherapy," Society for Minimally Invasive Therapy, 1995, vol. 4(Suppl 1):40 (abstr).

Knaut et al., "Intraoperative Microwave Ablation for Curative Treatment of Atrial Fibrillation in Open Heart Surgery—The MICRO–STAF and MICRO–PASS Pilot Trial", *The Thoracic and Cardiovascular Surgeon*, vol. 47, Aug. 1999 (Supplement), pp. 379–384.

Hindricks et al., "Antiarrhythmic Surgery for Treatment of Atrial Fibrillation—New Concepts", *The Thoracic and Cardiovascular Surgeon*, vol. 47, Aug. 1999 (Supplement), pp. 365–369.

* cited by examiner

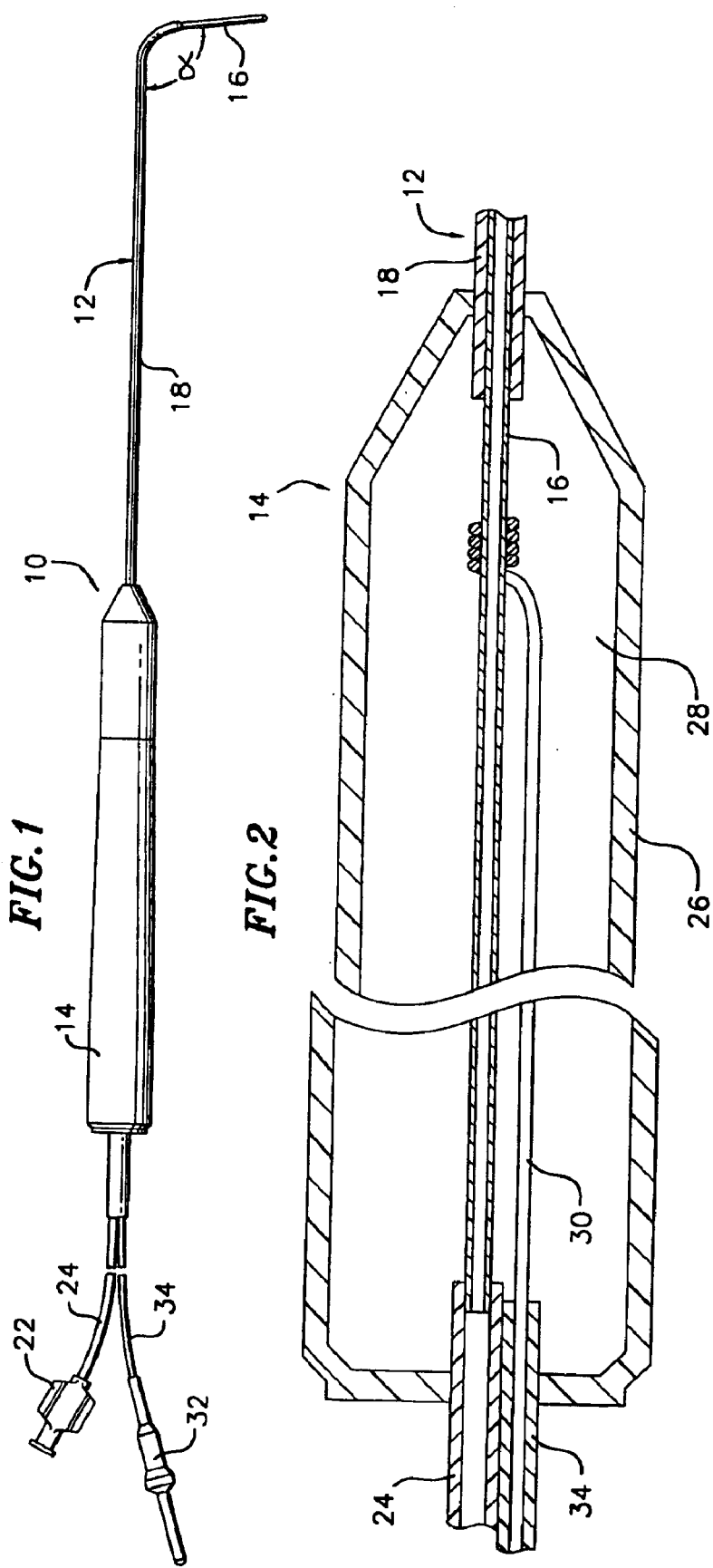

IRRIGATION PROBE FOR ABLATION DURING OPEN HEART SURGERY

FIELD OF THE INVENTION

The present invention is directed to an irrigation ablation probe for use during open heart surgery.

BACKGROUND OF THE INVENTION

Atrial fibrillation is a common sustained cardiac arrhythmia and a major cause of stroke. This condition is perpetuated by reentrant wavelets propagating in an abnormal atrial-tissue substrate. Various approaches have been developed to interrupt wavelets, including surgical or catheter-mediated atriotomy. It is believed that to treat atrial fibrillation by radio-frequency ablation using a catheter, continuous linear lesions must be formed to segment the heart tissue. By segmenting the heart tissue, no electrical activity can be transmitted from one segment to another. Preferably, the segments are made too small to be able to sustain the fibrillatory process.

It has been found that over 60% of patients with mitral valve problems also have atrial fibrillation. Moreover, patients undergoing open heart surgery commonly develop atrial fibrillation during the surgery, and thus it would be useful to address this problem during the surgery. Accordingly, under certain circumstances it may be desirable to treat atrial fibrillation during open heart surgery, for example, when a patient is undergoing a mitral valve replacement or repair procedure. Accordingly, a need exists for devices and methods for treating atrial fibrillation during open heart surgery.

SUMMARY OF THE INVENTION

The present invention is directed to an irrigation ablation probe for treating atrial fibrillation during open heart surgery. The probes of the present invention are also useful for other ablation procedures, particularly where irrigation of the ablation site is desired, such as for treating ventricular tachycardia. The invention is also directed to novel methods for treating atrial fibrillation with the probe of the invention. In accordance with the present invention, the probe comprises a rigid probe body and an irrigated ablation electrode, which provides cooling and irrigation in the region of the tissue being ablated.

In one embodiment, the invention is directed to an irrigation ablation probe comprising a generally rigid probe body having proximal and distal ends. The probe body has an ablation electrode at its distal end having at least one irrigation opening through which fluid can pass. An infusion tube having proximal and distal ends extends through the probe body for introducing fluid into the ablation electrode.

In another embodiment, the invention is directed to an irrigation ablation probe. The probe comprises a generally rigid probe body and a handle. The probe body has proximal and distal ends and comprises an ablation electrode at its distal end. The ablation electrode has at least one irrigation opening through which fluid can pass. The handle is mounted to the proximal end of the probe body. An infusion tube having proximal and distal ends extends through the probe body for introducing fluid into the ablation electrode. In a particularly preferred embodiment, the generally rigid probe body comprises a tubular electrode and a non-conductive sheath covering a portion of the tubular electrode. In another preferred embodiment, the generally rigid probe body comprises tubing having proximal and distal ends and at least one lumen extending therethrough. A tip electrode is mounted at the distal end of the tubing. The tip electrode has at least one irrigation opening through which fluid can pass. The probe body further comprises means for introducing fluid through the irrigation opening(s) of the tip electrode and a stiffening wire extending through a lumen of the tubing. A preferred means for introducing fluid comprises an infusion tube that extends through a lumen of the tubing with the distal end of the infusion tube in fluid communication with the one irrigation opening(s) in the tip electrode.

In still another embodiment, the invention is directed to an irrigation ablation probe comprising a generally rigid probe body and a handle mounted to the proximal end of the probe body. The probe body has an ablation electrode at its distal end. The generally rigid probe body comprises a malleable material.

In yet another embodiment, the invention is directed to a method for treating atrial fibrillation in a patient. The method comprises opening the heart of the patient and ablating at least one linear lesion in the heart tissue using an irrigation probe as described above.

DESCRIPTION OF THE DRAWINGS

These and other features and advantages of the present invention will be better understood by reference to the following detailed description when considered in conjunction with the accompanying drawings wherein:

FIG. 1 is a side view of an embodiment of an irrigation ablation probe according to the invention.

FIG. 2 is a side cross-sectional view of the handle of the irrigation ablation probe of FIG. 1.

DETAILED DESCRIPTION

Figure 3:
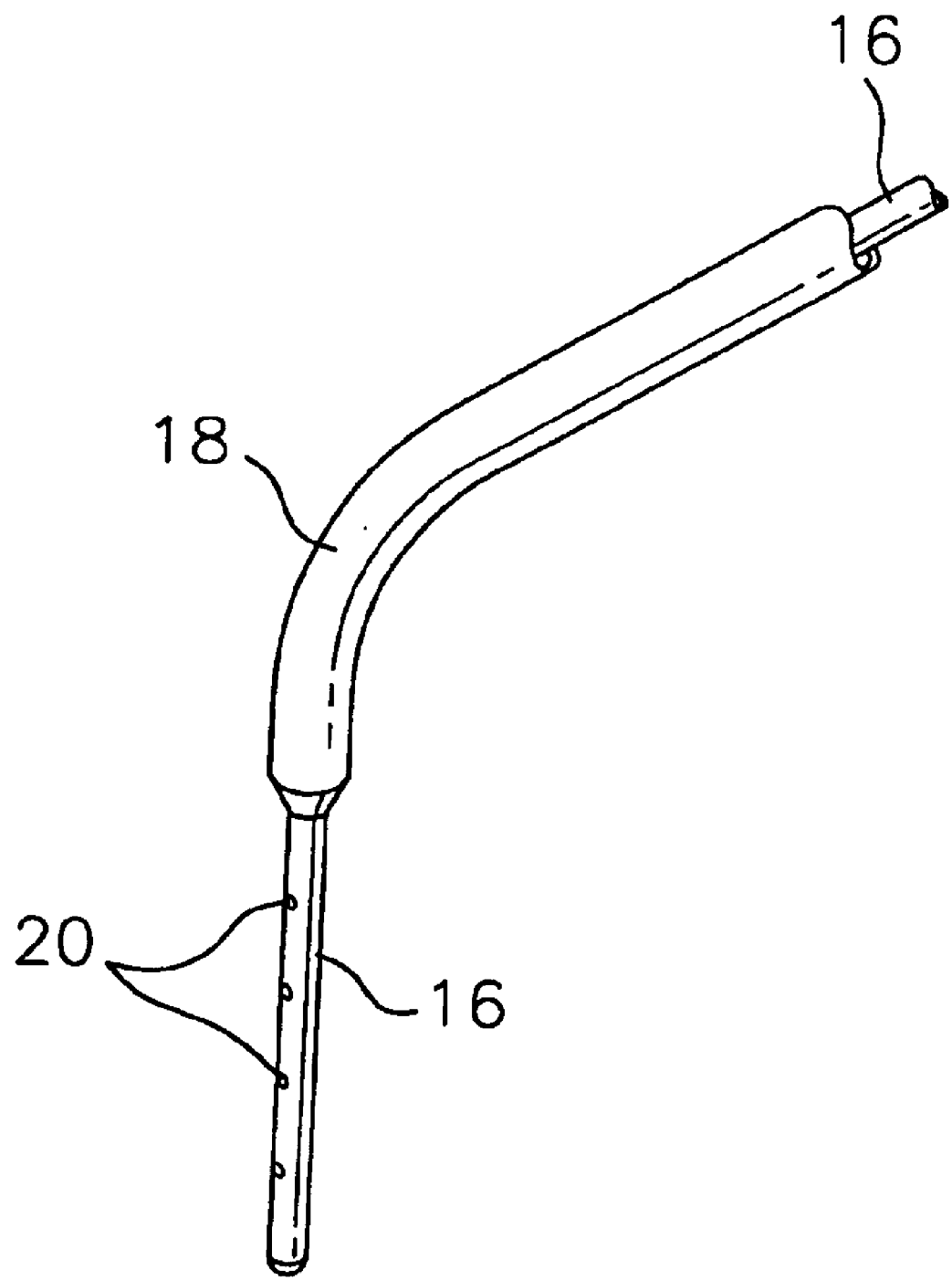
FIG. 3 is a perspective view of the distal end of the irrigation ablation probe of FIG. 1.

The present invention is directed to an irrigation ablation probe for use during open heart surgery. In one embodiment, as shown in FIGS. 1 and 2, the irrigation ablation probe 10 comprises a probe body 12 mounted to a handle 14. The probe body 12 comprises a tubular electrode 16, having proximal and distal ends, covered over a proximal portion of its length by a non-conductive covering or sheath 18. The tubular electrode 16 extends the entire length of the probe body 12, the proximal end of the tubular electrode extending into the handle 14 as described in more detail below. The probe body 12 preferably has a length (from the distal end of the handle to the distal end of the probe body) ranging from about 3.5 inches to about 12 inches, more preferably from about 5 to about 10 inches, still more preferably from about 7 to about 8 inches.

The tubular electrode 16 is made of a material that is generally rigid so that the probe body 12 cannot bend during ablation, such as, for example, stainless steel (preferably 304VSS) or nitinol. Preferably the tubular electrode 16 has an inner diameter ranging from about 0.40 inch to about 0.80 inch, more preferably about 0.047 inch, and an outer diameter ranging from about 0.50 inch to about 0.90 inch, more preferably about 0.059 inch. If desired, the tubular electrode 16 can be heat-treated so that it is malleable enough to be bent by a physician to a desired shape but still rigid enough that it will not bend in use during an ablation procedure. For example, for 304VSS stainless steel, the material is heated to about 800° F. with electrical current or in a salt bath. The hollow interior of the tubular electrode 16 forms a lumen through which saline and the like may be infused during an ablation procedure, as described in more detail below.

The non-conductive sheath 18 extends from a proximal end inside the handle 14 to a distal end that is longitudinally spaced apart from the distal end of the tubular electrode 16. In this arrangement, the distal end of the tubular electrode 16 is exposed, i.e., not covered by the sheath 18, for ablating tissue. Preferably the length of the exposed portion of the tubular electrode 16 ranges from about 0.50 inch to about 1.5 inches, more preferably from about 0.75 inch to about 1.25 inches. The sheath 18 can be made of any suitable biocompatible non-conductive material, such as polyurethane.

In the embodiment depicted in FIGS. 1 to 3, the probe body 12 is bent near its distal ends at an angle α, with the exposed distal end of the tubular electrode 16 being generally straight. However, the probe body 12 can alternatively be straight along its entire length. The angle α preferably ranges from about 0° to about 270°, more preferably from about 60° to about 140°, still more preferably about 90°. The angle α depends on the location of the heart tissue to be ablated. If the tubular electrode 16 is malleable, the surgeon can bend the probe body 12 to adjust the angle α for a particular procedure.

In the depicted embodiment, the length of the probe body 12 is approximately 7 inches. The proximal section of the probe body 12, i.e., the portion extending from the handle 14, is approximately 5.5 inches. The length of the exposed distal portion of the tubular electrode 16, i.e., the portion not covered by the sheath 18, is approximately 1 inch.

As shown in FIG. 3, the exposed distal end of the tubular electrode 16 has a series of irrigation openings 20 for passage of a cooling fluid out through the electrode. The irrigation openings 20 can take any suitable shape, such as rectangular or oval slots or round holes. The irrigation openings 20 are preferably in the section of the exposed portion of the tubular electrode 16 that is to be in contact with the tissue during an ablation procedure to enhance the cooling of the ablation site.

Saline or other suitable fluid is introduced into the tubular electrode 16 through a luer hub 22 or the like at the proximal end of the probe 10. The luer hub 22 is connected to a flexible plastic tubing 24, e.g., made of polyimide. The plastic tubing 24 is attached to the proximal end of the tubular electrode 16, preferably within the handle 14, as shown in FIG. 2. Alternatively, the tubing 24 can be connected to a suction source (not shown) to permit aspiration of fluid from the region being ablated.

As shown in FIG. 2, the handle 14 comprises a housing 26 having a generally open interior 28. The tubular electrode 16 and sheath 18 extend into the distal end of the handle housing 26. In the depicted embodiment, the sheath 18 terminates a short distance proximal to the distal end of the housing 26. The tubular electrode 16 continues proximally beyond the sheath 18. The flexible plastic tubing 24 extends into the proximal end of the handle housing 26. The plastic tubing 24 is attached to the tubular electrode 16 within the open interior 28 of the handle, preferably at a point proximal to the proximal end of the sheath 18. The plastic tubing 24 can be attached to the tubular electrode 16 by any suitable means, for example, polyurethane glue. By this design, cooling fluid is introduced through the luer hub 22, though the plastic tubing 24, through the tubular electrode 16 and out the irrigation openings 20 in the exposed distal end of the tubular electrode.

An electrode lead wire 30 having proximal and distal ends is electrically connected at or adjacent its distal end to the tubular electrode 16. The proximal end of the lead wire 30 is attached to a connector 32 for connection to a suitable source of radio frequency energy. In the depicted embodiment, the lead wire 30 extends into the proximal end of the handle housing 26. Within the open interior 28 of the handle 14, the distal end of the lead wire 30 is wrapped around the portion of the tubular electrode 16 not covered by the sheath 18 and held in place by solder or the like. The portion of the lead wire 30 that extends outside the handle 14 is covered by a flexible plastic protective tubing 34, e.g., made of polyimide.

Figure 4:
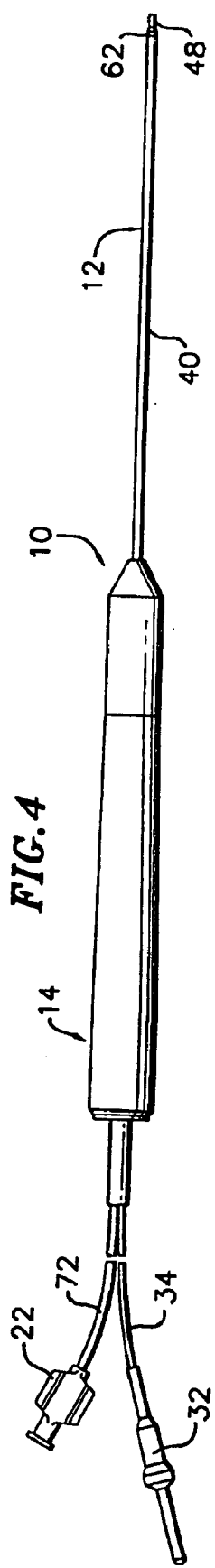
FIG. 4 is a side view of an alternative embodiment of an irrigation ablation probe according to the invention.
Figure 5:
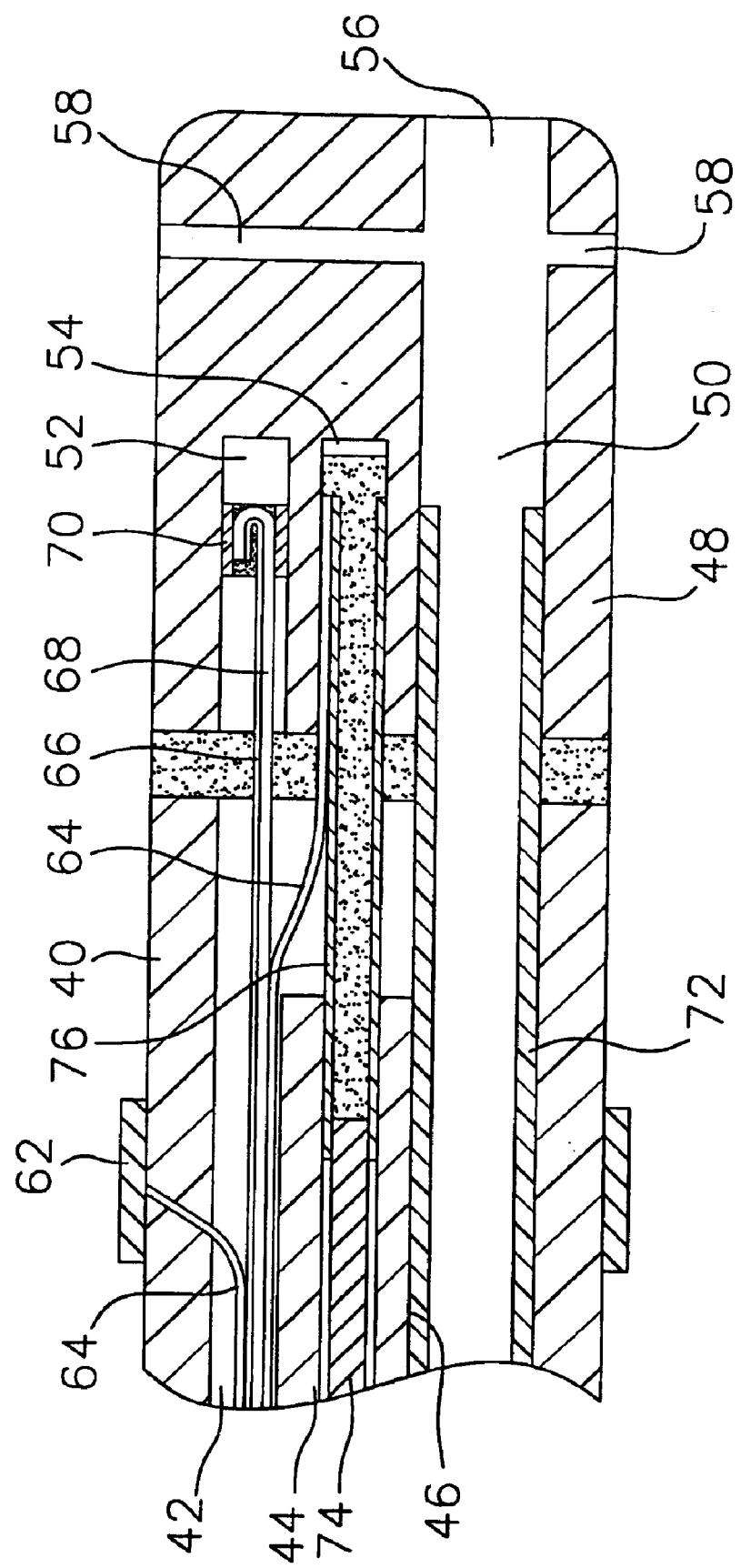
FIG. 5 is a side cross-sectional schematic view of the distal end of the irrigation ablation probe of FIG. 4, wherein the lumens are not shown to scale.
Figure 6:
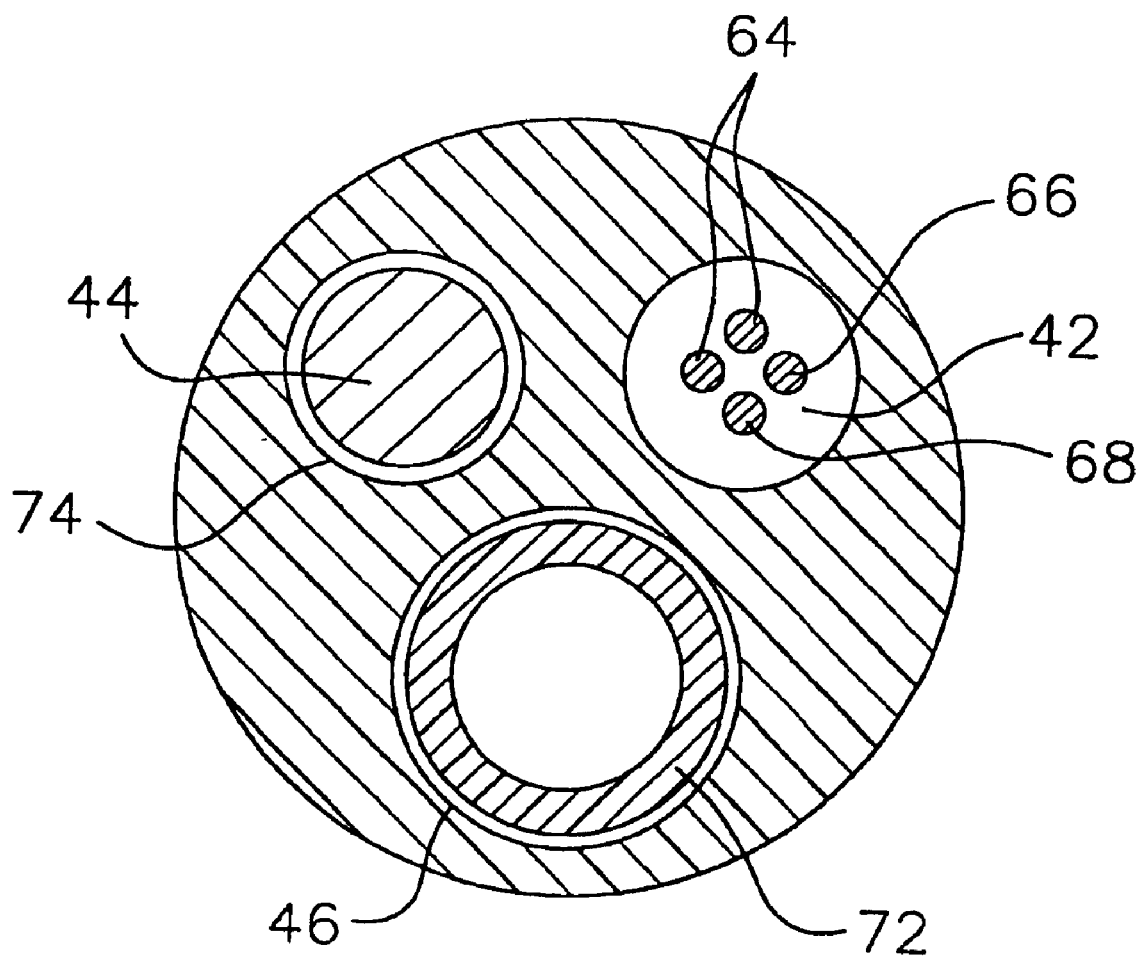
FIG. 6 is an end cross-sectional view of the distal end of the irrigation probe of FIG. 4.

An alternative embodiment of an irrigation ablation probe according to the invention is shown in FIGS. 4 to 6. The probe 10 comprises a probe body 12 and a handle 14. The probe body 12 comprises a non-conductive tubing 40 having proximal and distal ends. In a particularly preferred embodiment, the non-conductive tubing 40 comprises outer and inner plastic walls, e.g., of polyurethane or polyimide, surrounding an imbedded braided mesh of stainless steel or the like. Preferably the tubing has an outer diameter of less than 8 French, more preferably less than 7 French. The tubing 40 has three lumens 42, 44 and 46 extending along its length.

An irrigated tip electrode 48 is fixedly mounted on the distal end of the non-conductive tubing 40. Preferably the tip electrode 48 has a diameter about the same as the outer diameter of the to tubing 40 and an exposed length, i.e., the length extending outside of the tubing, ranging from about 2 mm to about 10 mm. As illustrated in FIG. 5, the tip electrode 48 is generally solid, having a fluid passage 50 and first and second blind holes 52 and 54 that correspond in size and location to the three lumens 46, 42 and 44, respectively, in the non-conductive tubing 40. In the embodiment shown, the fluid passage 50 comprises a longitudinal branch 56 and six transverse branches 58 that extend transversely from near the distal end of the longitudinal branch to the outer surface of the tip electrode 48. Itis understood that the configuration of the fluid passage 50 may vary as desired. For example, the fluid passage 50 may form a longitudinal hole that extends out the distal end of the tip 219 electrode 48 without transverse branches, or the tip electrode 48 may be porous enough to allow fluids to pass to the outer surface of the tip electrode, the interconnecting pores forming the fluid passage. Examples of suitable porous electrodes for use in the present invention are described in U.S. Patent Application entitled "Porous Irrigated Tip Electrode Catheter", by inventors Michele Fung and Shawn Moaddeb, filed concurrently herewith, the disclosure of which is incorporated herein by reference.

The tip electrode 48 can be attached to the non-conductive tubing 40 in any suitable manner. In the depicted embodiment, the tip electrode 48 is attached to the tubing 40 by polyurethane glue or the like. The wires and tubes that extend into the tip electrode 48, discussed more below, help to keep the tip electrode in place on the tubing 40. However, any other means for fixedly mounting the tip electrode 48 on the distal end of the tubing 40 can also be used.

In the embodiment shown, a mapping ring electrode 62 is mounted on the tubing 40 proximal to the tip electrode 48.

It is understood that the presence and number of ring electrodes may vary as desired. The ring electrode 62 is slid over the tubing 40 and fixed in place by glue or the like.

The tip electrode 48 and ring electrodes 62 can be made of any suitable material, and are preferably machined from platinum-iridium bar (90% platinum/10% iridium).

The tip electrode 48 and ring electrode 62 are each connected to a separate lead wire 64. The lead wires 64 extend through the first lumen 42 of tubing 40 and through the handle 14. The lead wires 64 terminate at their proximal end in a connector 32 that may be plugged into an appropriate monitor and/or source of radio frequency energy. The portion of the lead wires 64 extending out the proximal end of the handle 14 are enclosed within a protective tubing 34, which can be made of any suitable material, preferably polyimide.

The lead wires 64 are attached to the tip electrode 48 and ring electrode 62 by any conventional technique. Connection of a lead wire 64 to the tip electrode 48 is accomplished, for example, by soldering the lead wire 64 into the second blind hole 54 in the tip electrode.

Connection of a lead wire 64 to the ring electrode 62 is preferably accomplished by first making a small hole through the tubing 40. Such a hole can be created, for example, by inserting a needle through the tubing 40 and heating the needle sufficiently to form a permanent hole. A lead wire 64 is then drawn through the hole by using a microhook or the like. The ends of the lead wire 64 are then stripped of any coating and soldered or welded to the underside of the ring electrode 62, which is then slid into position over the hole and fixed in place with polyurethane glue or the like.

A temperature sensing means is provided for the tip electrode 48 and, if desired, the ring electrode 62. Any conventional temperature sensing means, e.g., a thermocouple or thermistor, may be used. With reference to FIG. 5, a preferred temperature sensing means for the tip electrode 48 comprises a thermocouple formed by a wire pair. One wire of the wire pair is a copper wire 66, e.g., a number 38 copper wire. The other wire of the wire pair is a constantan wire 68, which gives support and strength to the wire pair. The wires 66 and 68 of the wire pair are electrically isolated from each other except at their distal ends where they contact and are twisted together, covered with a short piece of plastic tubing 70, e.g., polyimide, and covered with epoxy. The plastic tubing 70 is then attached in the first blind hole 52 of the tip electrode 48 by polyurethane glue or the like. The wires 66 and 68 extend through the first lumen 42 in the non-conductive tubing 40. The wires 66 and 68 then extend out through the handle 14 and to a connector (not shown) connectable to a temperature monitor (not shown).

Alternatively, the temperature sensing means may be a thermistor. A suitable thermistor for use in the present invention is Model No. AB6N2-GC14KA143E/37C sold by Thermometrics (New Jersey).

An infusion tube 72 is provided for infusing fluids, e.g., saline, to cool the tip electrode 48. The infusion tube 72 may also be used to infuse drugs or to collect tissue or fluid samples. The infusion tube 72 may be made of any suitable material, and is preferably made of polyimide tubing. The infusion tube 72 has proximal and distal ends, with its distal end mounted in the fluid passage 50 of the tip electrode 48 by any suitable method, e.g., by polyurethane glue or the like. The infusion tube 72 extends from the tip electrode 48, through the third lumen 46 of the tubing 40, and through the handle 14. The proximal end of the infusion tube 72 ends in a luer hub 22 or the like.

A stiffening wire 74, having proximal and distal ends, is mounted in the second lumen 44 of the tubing 40. The stiffening wire 74 is made of a rigid metal or plastic material, preferably stainless steel, to prevent the probe body 12 from bending during an ablation procedure. If desired, the stiffening wire 74 can be heat-treated so that it is malleable and can be bent to a desired shape before use, but still rigid enough that it will not bend in use during an ablation procedure. A non-conductive tube 76, preferably made of polyimide, is attached to the distal end of the stiffening wire 74 for mounting the stiffening wire in the tip electrode 48. The non-conductive tube 76 extends out the second lumen 44 and into the second blind hole 54 in the tip electrode 48, and is secured in place by polyurethane glue or the like. The non-conductive tube 76, along with the infusion tube 72, lead wires 64, and thermocouple wires 66 and 68, helps to maintain the tip electrode 48 in place on the tubing 40. As would be recognized by one skilled in the art, the stiffening wire 74 could be mounted in any other suitable way so long as the stiffening wire, if made of metal, is not in electrical connection with the tip electrode 46. The proximal end of the stiffening wire 74 terminates in the handle 14 or near the proximal end of the probe body 12.

The tubular electrode 38 is then used to form continuous linear lesions by ablation. As used herein, a linear lesion refers to any lesion, whether curved or straight, between two anatomical structures in the heart that is sufficient to block a wavelet, i.e., forms a boundary for the wavelet. Anatomical structures, referred to as "atrial trigger spots", are those regions in the heart having limited or no electrical conductivity and are described in Haissaguerre et al., "Spontaneous Initiation of Atrial Fibrillation by Ectopic Beats Originating in the Pulmonary Veins", New England Journal of Medicine, 339:659–666 (Sep. 3, 1998), the disclosure of which is incorporated herein by reference. The linear lesions typically have a length of from about 1 cm to about 4 cm, but can be longer or shorter as necessary for a particular procedure.

The above described probes are for use during open heart surgery. During a procedure, the heart is opened and the irrigated electrode is used to form continuous linear lesions by ablation. As used herein, a linear lesion refers to any lesion, whether curved or straight, between two anatomical structures in the heart that is sufficient to block a wavelet, i.e., forms a boundary for the wavelet. Anatomical structures, referred to as "atrial trigger spots", are those regions in the heart having do limited or no electrical conductivity and are described in Haissaguerre et al., "Spontaneous Initiation of Atrial Fibrillation by Ectopic Beats Originating in the Pulmonary Veins", New England Journal of Medicine, 339:659–666 (Sep. 3, 1998), the disclosure of which is incorporated herein by reference. The linear lesions typically have a length of from about 1 cm to about 4 cm, but can be longer or shorter as necessary for a particular procedure. The above-described probe having a long tubular electrode is particularly useful for this procedure because it can create relatively long lesions. The probe depicted in FIGS. 4 to 6 above, having a smaller ablation electrode, is useful if the surgeon does not want to ablate as much tissue or wants to ablate a more precise lesion. The above-described probe having a malleable body is particularly useful if the surgeon needs to bend the probe to better ablate a desired region of tissue. Once the heart is closed, the surgeon can use the probe depicted in FIGS. 4 to 6, above, on the outside of the heart, not only to ablate, but to verify that the electrical conduction has been stopped using the mapping electrodes. As would be recognized by one skilled in the art, the probes of the present invention can be used during open heart surgery for other ablation procedures as well.

The preceding description has been presented with reference to presently preferred embodiments of the invention.

Workers skilled in the art and technology to which this invention pertains will appreciate that alterations and changes in the described structure may be practiced without meaningfully departing from the principal, spirit and scope of this invention.

Accordingly, the foregoing description should not be read as pertaining only to the precise structures described and illustrated in the accompanying drawings, but rather should be read consistent with and as support to the following claims which are to have their fullest and fair scope.

What is claimed is:

1. An irrigation ablation probe comprising:
   an elongated probe body having a length between proximal and distal ends and comprising an elongated ablation electrode extending the length of the elongated probe body, wherein the elongated ablation electrode defines an inner cavity, the elongated ablation electrode having at least one irrigation opening through which fluid can pass from the inner cavity to the outside of the elongated ablation electrode, the ablation electrode being generally rigid from its proximal end to its distal end so that the ablation electrode cannot bend during ablation, and wherein the elongated ablation electrode has an exposed distal portion that is generally straight and forms an angle α greater than 0° with the remainder of the elongated probe body, the angle α being preformed;
   a sheath positioned on the elongated ablation electrode and configured to define the exposed distal portion, wherein the elongated ablation electrode has a length greater than a length of the sheath;
   means for introducing fluid into the inner cavity; and
   a handle mounted at the proximal end of the elongated probe body, the handle comprising a housing having a generally open interior receiving a proximal end of the elongated ablation electrode;
   wherein the elongated ablation electrode remains in a fixed position relative to the elongated probe body and the handle during operation of the probe.

2. An irrigation ablation probe according to claim 1, wherein the means for introducing fluid comprises an infusion tube attached to the proximal end of the elongated ablation electrode.

3. An irrigation ablation probe according to claim 1, wherein the elongated generally rigid probe body comprises a malleable material.

4. An irrigation ablation probe according to claim 1, wherein the means for introducing fluid into the inner cavity comprises an infusion tube having proximal and distal ends and extending through the probe body.

5. An irrigation probe according to claim 4, wherein the infusion tube and the ablation electrode together comprises a single generally hollow body.

6. An irrigation ablation probe according to claim 1, wherein the exposed distal portion of the elongated ablation electrode is conductive around a full circumference of the exposed distal portion.

7. An irrigation ablation probe according to claim 6, wherein substantially the entire exposed distal portion of the elongated ablation electrode is conductive.

8. An irrigation ablation probe according to claim 1, wherein the angle α ranges from greater than 0° to about 270°.

9. An irrigation ablation probe according to claim 1, wherein the angle α ranges from about 600 to about 140°.

10. An irrigation ablation probe according to claim 1, wherein the angle α us about 90°.

11. An irrigation ablation probe according to claim 1, wherein the at least one irrigation opening is located in the exposed distal portion of the elongated ablation electrode to be in contact with the tissue to be ablated.

12. An irrigation ablation probe according to claim 1, wherein a plurality of irrigation openings are located in the exposed distal portion of the elongated ablation electrode to be in contact with the tissue to be ablated.

13. An irrigation ablation probe according to claim 1, wherein the infusion tube and the elongated ablation electrode comprise a single generally hollow body.

14. An irrigation ablation probe comprising:
   an elongated probe body having a length between proximal and distal ends and comprising an elongated tubular ablation electrode extending the length of the elongated probe body, the elongated tubular ablation electrode having at least one irrigation opening through which fluid can pass to the outside of the elongated tubular ablation electrode, the elongated probe body being generally rigid from its proximal end to its distal end so that the body cannot bend during ablation, and wherein the elongated tubular ablation electrode is generally rigid and has an exposed distal portion is generally straight and forms an angle α greater than 0° with the remainder of the elongated probe body, the angle α being preformed;
   a non-conductive sheath positioned on the elongated tubular ablation electrode and configured to define the exposed distal portion, wherein the elongated ablation electrode has a length greater than a length of the sheath;
   a handle mounted to the proximal end of the elongated probe body, the handle comprising a housing having a generally open interior receiving a proximal end of the elongated ablation electrode; and
   an infusion tube having proximal and distal ends and extending through the elongated probe body for introducing fluid into the elongated tubular ablation electrode, the distal end of the infusion tube being attached to the elongated tubular ablation electrode;
   wherein the elongated ablation electrode remains in a fixed position relative to the elongated probe body and the handle during operation of the probe.

15. An irrigation ablation probe according to claim 14, wherein the elongated tubular ablation electrode forms the infusion tube.

16. An irrigation ablation probe according to claim 14, wherein the elongated tubular ablation electrode is made of stainless steel.

17. An irrigation ablation probe according to claim 14, wherein the elongated tubular ablation electrode has an inner diameter ranging from about 0.40 inch to about 0.80 inch and an outer diameter ranging from about 0.50 inch to about 0.90 inch.

18. An irrigation ablation probe according to claim 14, wherein the elongated tubular ablation electrode has an outer diameter ranging from about 0.50 inch to about 0.70 inch.

19. An irrigation ablation probe according to claim 14, wherein the elongated tubular ablation electrode has an inner diameter ranging from about 0.40 inch to about 0.60 inch.

20. An irrigation ablation probe according to claim 14, wherein the elongated tubular ablation electrode is made of a malleable material.

21. An irrigation ablation probe according to claim 14, wherein the proximal end of the elongated tubular ablation electrode is mounted in the handle.

22. An irrigation ablation probe according to claim 14, further comprising a flexible plastic tubing attached to the proximal end of the elongated tubular ablation electrode for introducing fluid into the elongated tubular ablation electrode.

23. An irrigation ablation probe according to claim 22, wherein the flexible plastic tubing is attached to the proximal end of the elongated tubular ablation electrode within the handle.

24. An irrigation ablation probe according to claim 14, wherein the at least one irrigation opening is located in the exposed distal portion of the elongated tubular ablation electrode to be in contact with the tissue to be ablated.

25. An irrigation ablation probe according to claim 14, wherein the elongated probe body has a length ranging from about 3.5 inches to about 12 inches.

26. An irrigation ablation probe according to claim 14, wherein the elongated probe body has a length ranging from about 5 inches to about 10 inches.

27. An irrigation ablation probe according to claim 14, wherein the elongated probe body has a length ranging from about 7 inches to about 8 inches.

28. An irrigation ablation probe according to claim 14, wherein the exposed portion of the elongated tubular ablation electrode has a length ranging from about 0.50 inch to about 1.5 inches.

29. An irrigation ablation probe according to claim 14, wherein the exposed portion of the elongated tubular ablation electrode has a length ranging from about 0.75 inch to about 1.25 inches.

30. An irrigation ablation probe according to claim 14, wherein the generally rigid probe body comprises:
    tubing having proximal and distal ends and at least one lumen extending therethrough, wherein the ablation electrode is mounted at the distal end of the tubing; and
    a stiffening wire extending through one of the at least one lumens of the tubing.

31. An irrigation ablation probe according to claim 30, wherein the infusion tube extends through one of the at least one lumens of the tubing, and wherein the distal end of the infusion tube is in fluid communication with at least one irrigation opening in the ablation electrode.

32. An irrigation ablation probe according to claim 14, wherein the generally rigid probe body comprises:
    tubing having proximal and distal ends and at least one lumen extending therethrough; wherein the ablation electrode is mounted at the distal end of the tubing;
    wherein the infusion tube extends through one of the at least one lumens of the tubing, and wherein the distal end of the infusion tube is in fluid communication with the at least one irrigation opening in the ablation electrode; and
    a stiffening wire extending through one of the at least one lumens of the tubing.

33. An irrigation probe according to claim 32, wherein the probe body has a length ranging from about 3.5 inches to about 12 inches.

34. An irrigation probe according to claim 32, wherein the probe body has a length ranging from about 5 inches to about 10 inches.

35. An irrigation probe according to claim 32, wherein the probe body has a length ranging from about 7 inches to about 8 inches.

36. An irrigation ablation probe according to claim 14, wherein the generally rigid probe body comprises:
    tubing having proximal and distal ends and first and second lumens extending therethrough; wherein the ablation electrode is mounted at the distal end of the tubing;
    wherein the infusion tube extends through the first lumen of the tubing, and wherein the distal end of the infusion tube is in fluid communication with the at least one irrigation opening in the ablation electrode; and
    a stiffening wire having proximal and distal ends that extends through the second lumen of the tubing.

37. An irrigation probe according to claim 36, wherein the stiffening wire is made of stainless steel.

38. An irrigation ablation probe according to claim 36, wherein the stiffening wire is made of a malleable material.

39. An irrigation ablation probe according to claim 36, wherein the at least one irrigation opening comprises a longitudinal passage extending out the distal end of the tip electrode.

40. An irrigation ablation probe according to claim 36, wherein the at least on irrigation opening comprises at least one transverse passage.

41. An irrigation ablation probe according to claim 36, wherein the tip electrode is porous.

42. An irrigation ablation probe according to claim 36, further comprising a temperature sensing means mounted in a blind hole in the tip electrode.

43. An irrigation probe according to claim 36, wherein the probe body has a length ranging from about 3.5 inches to about 12 inches.

44. An irrigation probe according to claim 36, wherein the probe body has a length ranging from about 5 inches to about 10 inches.

45. An irrigation probe according to claim 36, wherein the probe body has a length ranging from about 7 inches to about 8 inches.

46. An irrigation probe according to claim 14, wherein the infusion tube and the ablation electrode together comprise a single generally hollow body.

47. An irrigation ablation probe according to claim 14, wherein the exposed distal portion of the elongated tubular ablation electrode is conductive around a full circumference of the exposed portion.

48. An irrigation ablation probe according to claim 47, wherein substantially the entire exposed portion of the elongated tubular ablation electrode is conductive.

49. An irrigation ablation probe according to claim 14, wherein the angle $\alpha$ ranges from greater than 0° to about 270°.

50. An irrigation ablation probe according to claim 14, wherein the angle $\alpha$ ranges from about 60° to about 140°.

51. An irrigation ablation probe according to claim 14, wherein the angle $\alpha$ is about 90°.

52. An irrigation ablation probe according to claim 14, wherein the infusion tube and the elongated tubular ablation electrode comprise a single generally hollow body.

53. A method for treating atrial fibrillation in a patient comprising:
    opening the heart of the patient; and ablating at least one linear lesion in the heart tissue using an irrigation probe as recited in claim 1.

54. A method for treating atrial fibrillation in a patient comprising:
    opening the heart of the patient; and
    ablating at least one linear lesion in the heart tissue using an irrigation probe as recited in claim 14.

55. A method for treating atrial fibrillation in a patient comprising:
    opening the heart of the patient; and
    ablating at least one linear lesion in the heart tissue using an irrigation probe as recited in claim 32.

56. A method for treating atrial fibrillation in a patient comprising:
    opening the heart of the patient; and
    ablating at least one linear lesion in the heart tissue using an irrigation probe as recited in claim 46.

* * * * *